US005644133A

United States Patent [19]
Didomenico et al.

[11] Patent Number: 5,644,133
[45] Date of Patent: Jul. 1, 1997

[54] REMOTE VEHICLE EMISSION ANALYZER WITH LIGHT CONVEYANCE TO DETECTORS THROUGH FIBER OPTIC LIGHT TUBES

[75] Inventors: John Didomenico; Dennis L. Smith; James H. Johnson, all of Tucson, Ariz.

[73] Assignee: Envirotest Systems, Corp., Tuscon, Ariz.

[21] Appl. No.: 506,476

[22] Filed: Jul. 25, 1995

[51] Int. Cl.⁶ .................................................. G01N 21/00
[52] U.S. Cl. ................ 250/338.5; 250/347; 250/339.13; 250/372; 250/236; 356/437; 356/438
[58] Field of Search ................... 250/372, 338.5, 250/339.13, 343, 373, 347, 353, 235, 236; 356/436, 437, 438

[56] References Cited

U.S. PATENT DOCUMENTS

| | | | |
|---|---|---|---|
| 5,210,702 | 5/1993 | Bishop et al. | 250/338.5 |
| 5,254,858 | 10/1993 | Wolfman et al. | 250/338.5 |
| 5,319,199 | 6/1994 | Stedman et al. | 250/338.5 |
| 5,319,200 | 6/1994 | Rosenthal et al. | 250/353 |
| 5,401,967 | 3/1995 | Stedman | 250/338.5 |

Primary Examiner—Michael J. Tokar
Assistant Examiner—Virgil O. Tyler
Attorney, Agent, or Firm—Jay H. Maioli

[57] ABSTRACT

A mechanical optical system scans a light beam that has passed through an automobile exhaust plume onto a plurality of detectors by using fiber optic tubes in an array that is mounted close to a rotating mirror. First ends of the fiber optic tubes are in an array adjacent the mirror and second ends of the fiber optic tubes feed the scanned light beam onto respective detectors that detect various gaseous components in the vehicle exhaust. Using the fiber optic tubes eliminates the need for secondary mirrors and reduces the requirement for highly accurate optical alignment among the components of the system.

16 Claims, 3 Drawing Sheets

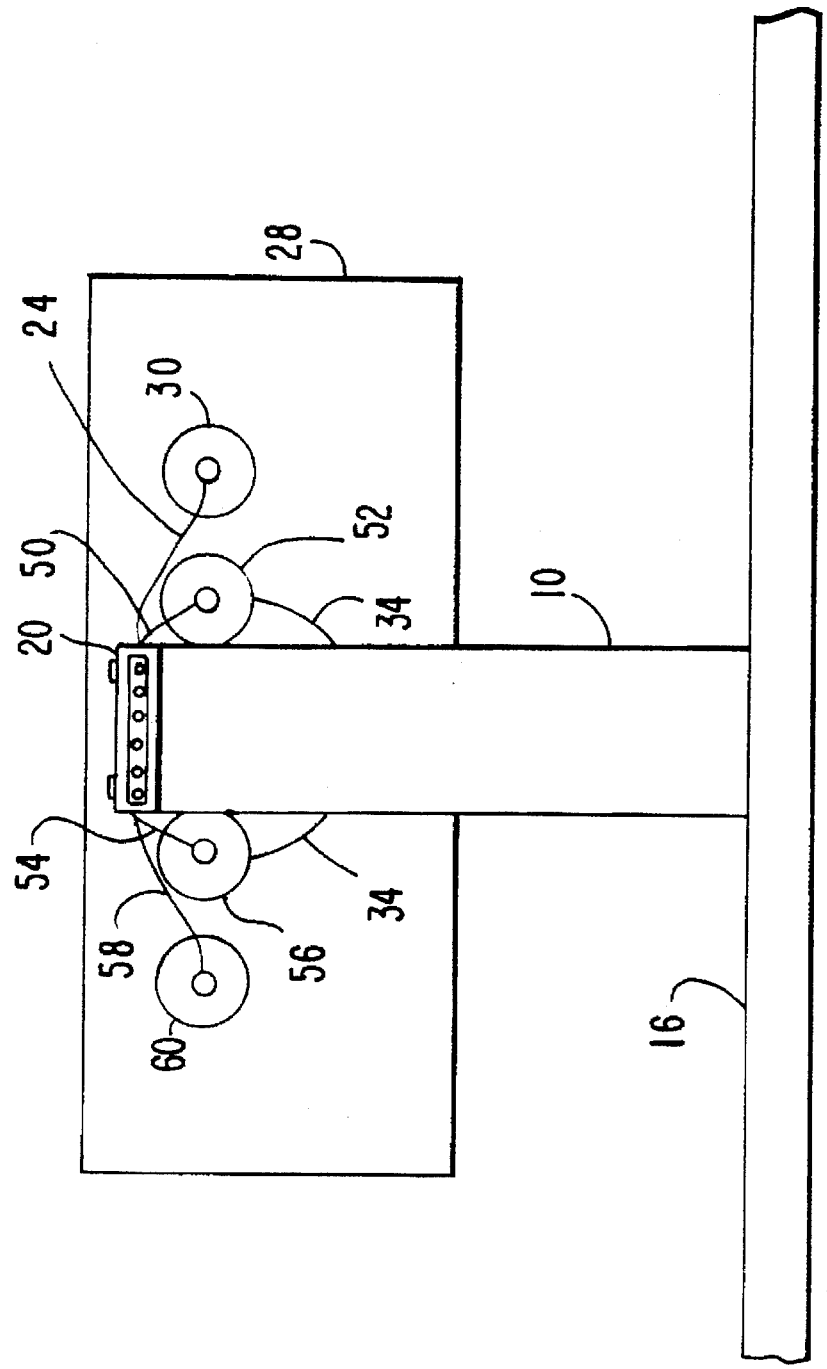

REMOTE VEHICLE EMISSION ANALYZER WITH LIGHT CONVEYANCE TO DETECTORS THROUGH FIBER OPTIC LIGHT TUBES

BACKGROUND OF THE INVENTION

1. Field of the Invention

This invention relates generally to rotating mirror light scanners and, more particularly, to rotating mirror light scanners used in remote vehicle emission analyzers.

2. Description of the Background

In view of the increasing concern with the degradation of the environment caused by motor vehicle emissions, there have been developed several systems for remotely analyzing the exhaust emissions of a motor vehicle as that vehicle drives through or passes a remote analyzing station. Typically, a light beam is directed across the roadway so that the beam of light passes through the plume of the vehicle exhaust and falls on several detector units that detect the levels of various gaseous components of the vehicle exhaust. In a known system only one light beam is used to intercept the vehicle exhaust plume, and that beam is scanned using an optical assembly onto a number of detector units arranged generally in the same housing and usually on the opposite side of the road from the light beam emitting assembly. The single beam can be caused to impinge successively on the several detectors using a flying spot scanner comprised of a multifaceted, rotating mirror. The beam, after having passed through the vehicle exhaust plume, is directed by a primary mirror onto the rotating mirror and as the mirror undergoes its rotational translation the beam is caused to be scanned onto a number of secondary mirrors that reflect their light beams onto respective detector units. The detector units are arranged side-by-side and at the same horizontal level, and the secondary mirrors are mounted around 8–10 inches from the rotating mirror.

This system works well in principle, however, it is difficult to set up because all of the components must be accurately aligned optically, in order for the beam to fall fully on each detector. In addition, optical misalignments and mechanical vibrations cause noise in the output signals of the detectors. Also, as in any optical system, the intensity of the light is diminished by action of the various optical elements so that the detector output signals may be of such a low level as to be susceptible to electrical noise as well.

Furthermore, the more times light is reflected in a design the more susceptible that design is to mechanical vibrations. Because the secondary mirrors are located 8 inches from the spinning mirror, the light at that point in the system is diluted, diffused, and susceptible to mechanical vibration. Also, because of the necessary optical alignment the secondary mirrors are partially blocked by the detectors and the mounting arrangement.

Light focused by the secondary mirrors onto the respective detector elements is non-homogeneous. This exacerbates signal noise level when slight movements in the system occur. Furthermore, as in any optical system, very precise alignment is required for successful operation.

Representative of previously proposed systems for use in scanning a light beam onto a number of detectors are the systems shown in U.S. Pat. Nos. 5,210,702 and 5,343,043.

OBJECTS AND SUMMARY OF THE INVENTION

Accordingly, it is an object of the present invention to provide a system for scanning a light beam onto a number of detectors in which the above-noted defects inherent in the previously proposed systems are eliminated.

Another object of this invention is to provide a remote vehicle emission analyzer in which a light beam is scanned onto a number of detectors using a rotating mirror and fiber optic light tubes.

In accordance with an aspect of the present invention, a number of fiber optic light tubes are arranged quite closely to the rotating mirror with each individual light tube being led off to a respective detector. The use of secondary mirrors is eliminated. The detectors may include a photo-multiplier tube for use in detecting nitrous oxide levels, as well as photovoltaic cells for detecting other gases. By utilizing the fiber optic tubes, the secondary mirrors are eliminated and alignment of the detectors relative to the light being scanned by the rotating mirror is eliminated. In addition, the signal level output from the detectors can be increased because the amount of light available to impinge on each detector is maximized.

The above and other objects, features, and advantages of the present invention will become apparent from the following detailed description of illustrative embodiments thereof to be read in conjunction with the accompanying drawings in which like references numerals indicate the same or similar elements.

BRIEF DESCRIPTION OF THE DRAWINGS

FIG. 3 is a front elevational view of the light beam scanning system of FIG. 1.

DETAILED DESCRIPTION OF PREFERRED EMBODIMENTS

Figure 1:
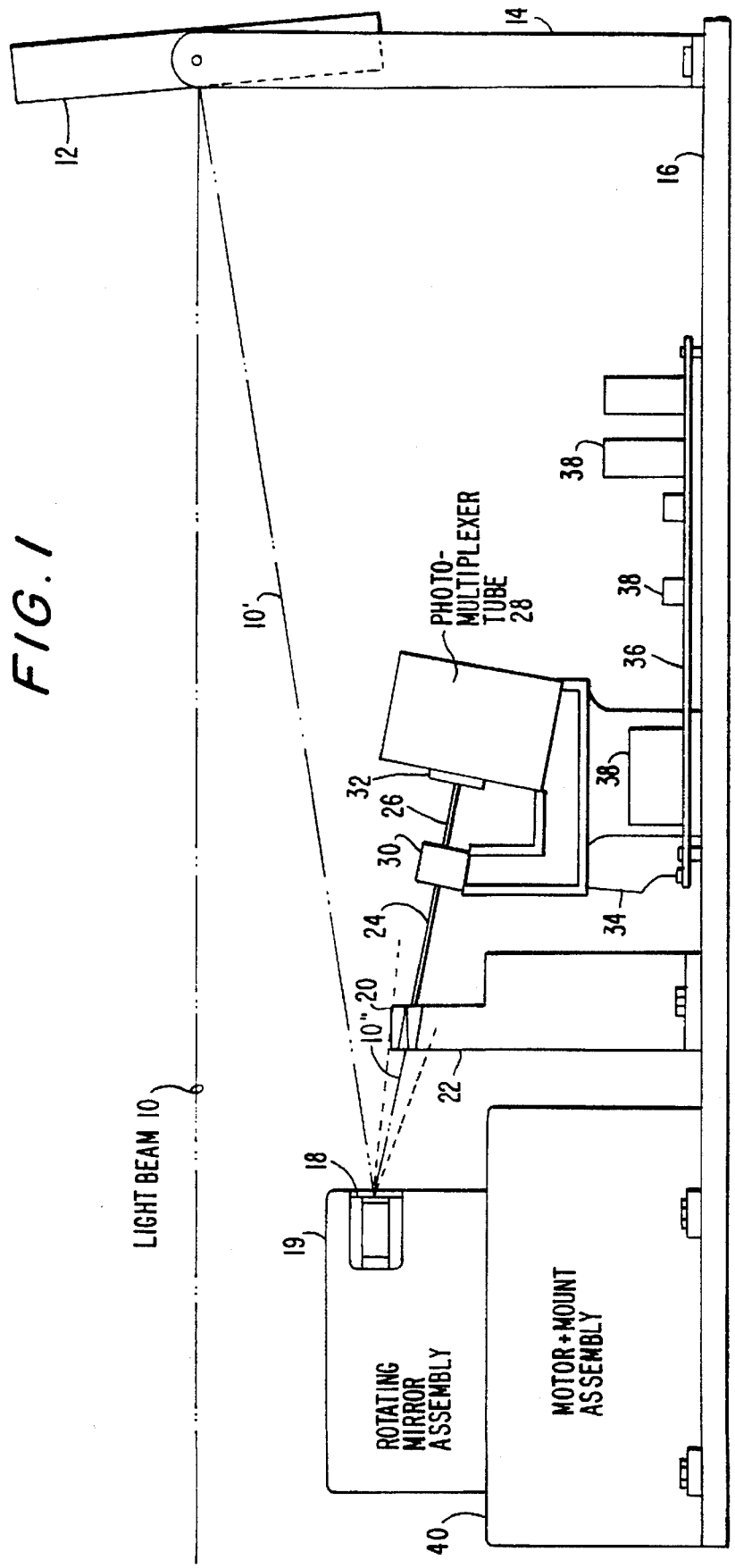
FIG. 1 is a side elevational view of a light beam scanning system using fiber optic tubes according to an embodiment of the present invention.

The embodiment of the present invention as shown in FIG. 1 is intended for use in a system that detects various gaseous and particulate components in the exhaust emission of an automobile by passing a light beam through the exhaust plume of the motor vehicle on the highway. Such a light beam includes ultraviolet wavelength radiation and infrared wavelength radiation and is shown at 10 in FIG. 1. The light beam 10 is directed to pass through the vehicle exhaust and impinge on a primary mirror 12. The primary mirror 12 is pivotally mounted on a support 14 that is attached to a so-called optical bench 16 that forms the base of the system of FIG. 1. The primary mirror 12 can be pivoted during system set up so that the light beam 10 is reflected from the primary mirror 12 to fall onto a mirror 18 of a rotating mirror assembly 19.

In the position of the rotating mirror assembly 19 shown in FIG. 1, the initially reflected light beam 10' is reflected again as light beam 10" onto a fiber optic tube array 20 mounted on an uppermost portion of a support 22 that is mounted on the base 16. The fiber optic tube array 20 is arranged to be 2–3 inches from the surface of the mirror 18. The fiber optic tube array 20 includes a number of fiber optic tubes, one of which is shown at 24 in FIG. 1 and another of which is shown at 26. Each fiber optic tube in the array 20 is only 2–3 millimeter in diameter so that the tubes in the array 20 can be closely arranged. In this way, the mirror 18 sprays the light beam onto the ends of the fiber optical light tubes in the array 20.

The fiber optic tube 26 is connected at one end to a photo multiplier tube 28 and is mounted at the other end at the fiber optic array 20. The fiber optic tube 24 is connected at one end to a detector 30 and is mounted at the other end at the fiber optical array 20.

Figure 2:
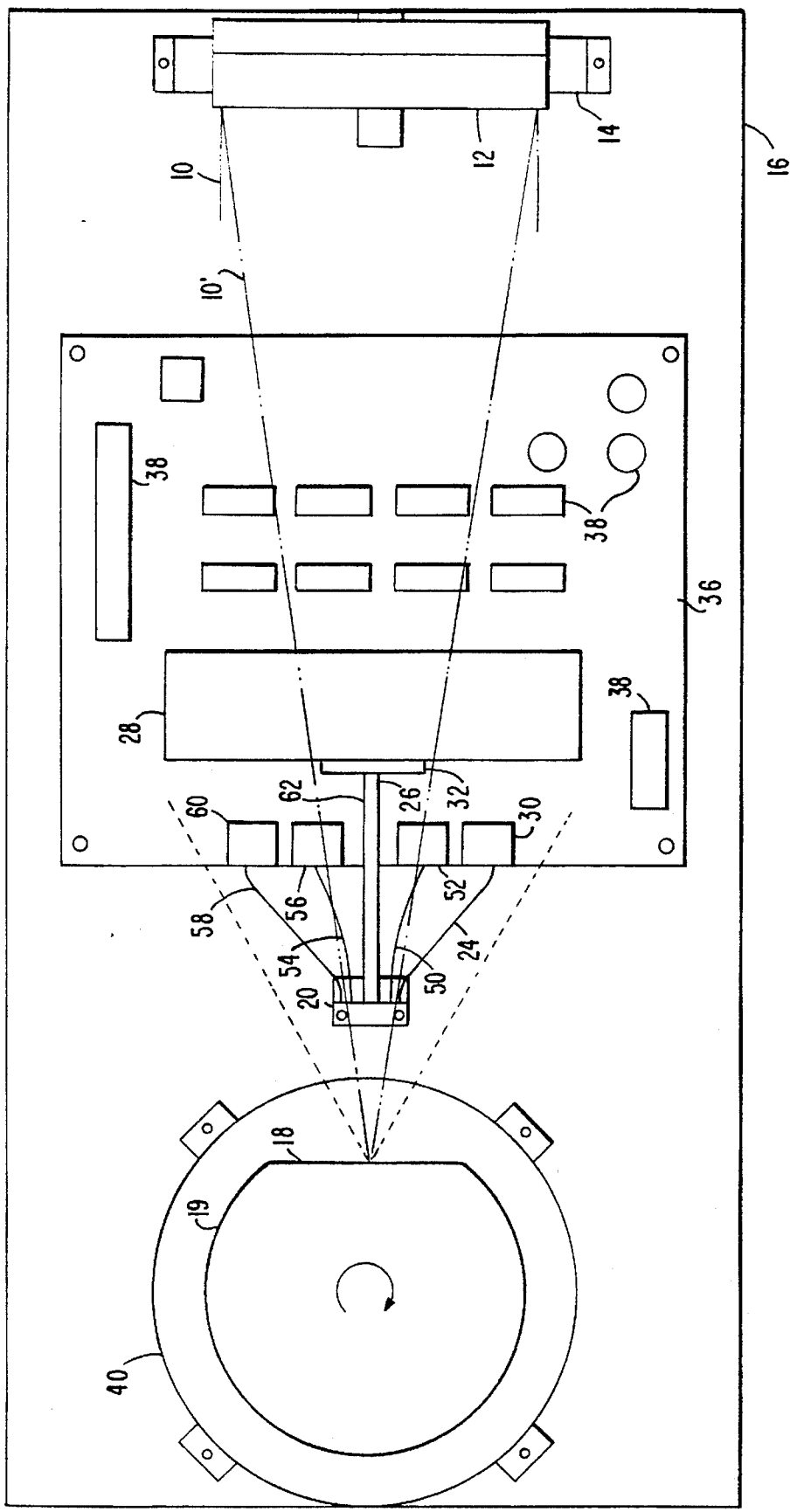
FIG. 2 is a top, plan view of the system of FIG. 1.

As shown in FIG. 2, in this embodiment there are a number of fiber optic tubes connected to a number of detectors. In fact, there are two fiber optic tubes used to feed the light to the photomultiplier. The photomultiplier 28 is provided to detect the amount of nitrous oxide $NO_x$ in the vehicle exhaust by detecting changes in the ultraviolet wavelength portion of the light beam 10. In that regard, an optical ultraviolet filter 32 is placed between the end of the fiber optic tube 26 and the input grid of the photo-multiplier tube 28.

Referring back to FIG. 1, the electrical output signals from the detector 30 and the photo-multiplier tube 28 are fed by an electrical cable 34 to a printed circuit board 36 that has various electrical components mounted thereon, which components are shown generally at 38. The output of the printed circuit board assembly 36 can be connected to a suitable microcomputer or the like to store and analyze the results of the vehicle exhaust emission detection. The rotating mirror assembly 19 is arranged on top of a motor and mount assembly 40 that is also fixed to the base 16. The motor, not shown drives the mirror assembly 19 to rotate. Although only one mirror 18 is shown, the rotating mirror assembly could include a multifaceted mirror, such as a polygon.

FIG. 2 is a top plan view of the embodiment of the present invention shown in FIG. 1, and in FIG. 2 the arrangement of the fiber optic head assembly 19 and the various fiber optic tubes, detectors, and the like are shown more clearly. More specifically, in addition to fiber optic tube 24 connected to detector 30, another fiber optic tube 50 is connected to another detector 52, another fiber optic tube 54 is connected to another detector 56, and another fiber optic tube 58 is connected to another detector 60. Each of these detectors 30, 52, 56, 60 is set up to detect a different gas or particle making up the exhaust plume through which the light beam 10 has passed. Each of these detectors 30, 52, 56, 60 can be a photovoltaic cell, with an optical filter (not shown) arranged between the end of the respective fiber optic tube and the inlet aperture of the detector.

The ends of the fiber optic tubes 24, 50, 26, 62, 54, 58 in the array 20 are between 2 to 3 inches from the surface of the mirror 18, and this results in more freedom of movement of the beam path, shown by the dashed lines in FIG. 2, without affecting the homogenous nature of the light as it passes down the tube. At 2 to 3 inches from the mirror 18 the reflected light if focused and homogeneous.

In addition to the fiber optic tube 26 that feeds the light to the photo-multiplier tube 28, another fiber optic tube 62 is also connected to the photo-multiplier tube 28 through the specially selected optical filter 32. This filter 32 is a narrow bandpass ultraviolet optical filter arranged at the entrance to the photomultiplier tube 28. This filter 32 prevents most of the infrared radiation from striking the photomultiplier tube 28. In addition, the photomultiplier tube 28 is chosen to be sensitive only to ultraviolet wavelengths and not to the longer wavelengths of visible light or to infrared wavelengths.

The functioning of the rotating mirror assembly 20 is shown more clearly in FIG. 2, wherein it can be appreciated that as the mirror 18 rotates the light beam 10' reflected by the primary mirror 12 is caused to be scanned across the fiber optic tube array 20. At 2 to 3 inches from the rotating mirror 18 there is substantial overspray of the light onto the fiber optic array 20, which permits mechanical movement of the system while minimizing vibration noise. Also, as seen in FIG. 1, the detectors are not located os as to block the light from the primary mirror.

In FIG. 3, a front view of the fiber optic tube array 20 and the photomultiplier tube 28 and detectors 30, 50, 54, 60 are shown. The view in FIG. 3 is what the mirror 18 would see including a mounting bracket 70 that is used to mount several detectors and the photo-multiplier tube 28 onto the base 16.

In the operation of the embodiment shown in FIGS. 1–3, the light beam 10 including ultraviolet and infrared wavelengths passing across the highway through the exhaust plume of the motor vehicle is directed by the primary mirror 12 and concentrated onto the spinning mirror 18. The light beam 10" directed by the spinning mirror 18 scans and overfills the fiber optic array 20, which is only 2 to 3 inches from the mirror 18. Thus, concentrated, homogeneous light enters each fiber optic tube 24, 50, 54, 58 and is directed by the respective tubes to the individual detector elements 30, 52, 56, 60, and the light falling on the fiber optic tubes 26, 62 is fed to the photo-multiplier tube 28. Because these fiber optic tubes need only be two to three millimeters in diameter, it is possible to locate the fiber ends very closely together and also quite close to the spinning mirror, for example, within two to three inches.

Thus, this embodiment of the present invention provides the advantages that the light is much more concentrated at a point closer to the spinning mirror and also by having such small dimension fiber optic tubes, there is much more freedom of movement in the beam path without affecting the homogenous nature of the light that travels down the fiber optic tube. In addition, the fiber optic tubes have the further advantage that they allow concentrated light to be conducted directly to the detector sensor element, with no requirement for beam focusing and with minimal signal loss. According to this embodiment the detector signal strength is increased, while at the same time beam alignment is simplified, and the light noise due to mechanical vibrations is substantially eliminated.

In the embodiment described above, there are situations where there is a single fiber optic tube connected to a single detector, as well as multiple fiber optic tubes going to a single detector, and in this embodiment that single detector with the multiple input tubes is the photomultiplier tube. Nevertheless, the invention is not limited to this specific configuration, and a single-end to multiple-end fiber optic tube could be connected to a multiple detectors having respective optical filters.

In regard to the specific make-up of these fiber optic tubes, there are two kinds of fibers that can be used for transmission of infrared light radiation in the 3.0 to 5.0 micron wavelength range. These two kinds of fibers are zirconium fluoride glass based fibers and chalcogenide glass based fibers. In the embodiment described hereinabove, the most suitable IR fiber is the glass clad fluoride glass fiber type, which has better than 80% transmission over a one meter length in this spectral range. These fibers can be made into fiber bundles of substantially any desired diameter. Glass clad fluoride glass fiber tubes are expensive and fragile when compared with the more conventionally known silica-glass quartz fibers used in fiber optic telecommunication cables.

In regard to fiber optic cables 26 and 62 that feed the light to the photomultiplier 28, the fibers used for this $NO_x$ gas detection must be capable of transmitting ultraviolet light in the 220 to 230 nanometer range. High OH-pure fused silica fibers are most suitable for this purpose, and these fibers are presently commercially available. The silica fibers can be assembled into relatively large diameter flexible bundles to deliver the light scanned by the rotating mirror onto the photomultiplier tube.

The science and knowledge concerning fiber optics is rapidly advancing, however, at present the infrared fibers currently available have relatively high attenuation in the 3.0 to 5.0 micron spectral range, for example, about 80% transmission per meter. In the embodiment shown and described hereinabove, the maximum length of the infrared fiber cables would be perhaps 0.2 meters. Over this distance, substantially 95% of the infrared power is transmitted to the detectors, with any surface reflections from the surface of the fiber optic cables being ignored as negligible.

The above is presented by way of example only and is not intended to limit such illustrative embodiment alone, and various modifications may be contrived without departing from the spirit or essential characteristics thereof, which are to be determined solely from the appended claims.

What is claimed is:

1. A system for conveying a transmitted light beam for analysis, comprising:

a primary mirror for reflecting the transmitted light beam in a first direction;

rotating mirror means arranged in said first direction relative to said primary mirror for scanning in a second direction the reflected light beam from the primary mirror;

a plurality of fiber optic tubes, first ends of said fiber optic tubes being closely arranged in a linear array and arranged in said second direction relative to said rotating mirror means, said array being separated from said rotating mirror means by a distance of two to three inches; and a plurality of light detector means having second ends of said fiber optic tubes arranged respectively thereon so that light scanned on said array is conducted to said plurality of light detector means, whereby the transmitted light beam is analyzed by said plurality of light detector means.

2. The system for conveying a transmitted light beam for analysis according to claim 1, wherein the transmitted light beam includes ultraviolet wavelengths and infrared wavelengths and one of said plurality of light detector means comprises a photomultiplier tube for detecting the ultraviolet wavelengths of the transmitted light beam.

3. The system for conveying a transmitted light beam for analysis according to claim 2, further comprising a narrow bandpass optical filter arranged between the second end of one of said fiber optic tubes and an entrance to said photomultiplier tube.

4. The system for conveying a transmitted light beam for analysis according to claim 1, wherein the transmitted light beam includes ultraviolet wavelengths and infrared wavelengths and one of said plurality of light detector means comprises a photomultiplier tube and a narrow bandpass optical filter at an entrance thereof for detecting the ultraviolet wavelengths of the transmitted light beam.

5. The system for conveying a transmitted light beam for analysis according to claim 4, wherein two of said plurality of fiber optic tubes have respective second ends arranged on said narrow bandpass optical filter at the entrance to said photomultiplier tube.

6. The system for conveying a transmitted light beam for analysis according to claim 4, wherein other ones of said plurality of light detector means comprise a plurality of photovoltaic cell means, each having an optical input connected to a respective second end of said plurality of fiber optic tubes.

7. Apparatus for conveying a transmitted light beam comprising:

a base;

a primary mirror mounted on said base for receiving and reflecting the transmitted light beam;

a rotating mirror mounted on said base for receiving a reflected light beam from said primary mirror and during rotation causing the reflected light beam to scan a predetermined angular sector;

a support mounted on said base at a position corresponding to said predetermined angular sector;

a plurality of fiber optic tubes having first ends closely arranged in a linear array and attached to an upper portion of said support so as to be separated from said rotating mirror by a distance of two to three inches and to be within said angular segment;

a bracket mounted on said base so that said support is between said rotating mirror and said bracket; and a plurality of light detector means mounted on said bracket and having second ends of said plurality of fibre optic tubes arranged at inputs thereof so that the reflected light beams from said primary mirror is scanned by said rotating mirror onto the first ends of the fiber optic tubes and conveyed therethrough to said plurality of light detector means.

8. The apparatus for conveying a transmitted light beam according to claim 7, wherein a height of said primary mirror above said base is greater than a height of said rotating mirror above said base.

9. The apparatus for conveying a transmitted light beam according to claim 8, wherein the height of said rotating mirror above said base is greater than a height above said base of said upper portion of said support whereat said array is arranged.

10. The apparatus for conveying a transmitted light beam according to claim 9, wherein the height of said upper portion of said support is greater than a height above said base of said bracket whereat said plurality of light detector means are mounted.

11. The apparatus for conveying a transmitted light beam according to claim 10, wherein one of said plurality of light detector means comprises a photomultiplier tube and said photomultiplier tube is mounted on said bracket at a location that is at a height above said base less than a height above said base whereat remaining ones of said plurality of light detector means are mounted.

12. The system for conveying a transmitted light beam for analysis according to claim 7, wherein the transmitted light beam includes ultraviolet wavelengths and infrared wavelengths and one of said plurality of light detector means comprises a photomultiplier tube for detecting the ultraviolet wavelengths of the transmitted light beam.

13. The system for conveying a transmitted light beam for analysis according to claim 12, further comprising a narrow bandpass optical filter arranged between the second end of one of said fiber optic tubes and an entrance to said photomultiplier tube.

14. The system for conveying a transmitted light beam for analysis according to claim 7, wherein the transmitted light beam includes ultraviolet wavelengths and infrared wavelengths and one of said plurality of light detector means comprises a photomultiplier tube and a narrow bandpass optical filter at an entrance thereof for detecting the ultraviolet wavelengths of the transmitted light beam.

15. The system for conveying a transmitted light beam for analysis according to claim 14, wherein two of said plurality of fiber optic tubes have respective second ends arranged on said narrow bandpass optical filter at the entrance to said photomultiplier tube.

16. The system for conveying a transmitted light beam for analysis according to claim 14, wherein other ones of said plurality of light detector means comprise a plurality of photovoltaic cell means, each having an optical input connected to a respective second end of said plurality of fiber optic tubes.

* * * * *